(12) United States Patent
Li et al.

(10) Patent No.: US 7,582,873 B2
(45) Date of Patent: Sep. 1, 2009

(54) METHOD AND APPARATUS FOR DETECTING THE TYPE OF ANESTHETIC GAS

(75) Inventors: Xinsheng Li, Nanshan (CN); Huiling Zhou, Nanshan (CN); Wei Zhang, Nanshan (CN); Jilun Ye, Nanshan (CN)

(73) Assignee: Shenzhen Mindray Bio-Medical Electronics Co., Ltd. (CN)

( * ) Notice: Subject to any disclaimer, the term of this patent is extended or adjusted under 35 U.S.C. 154(b) by 86 days.

(21) Appl. No.: 11/323,703

(22) Filed: Dec. 30, 2005

(65) Prior Publication Data

US 2006/0278829 A1     Dec. 14, 2006

(30) Foreign Application Priority Data

Jun. 10, 2005    (CN)    ................. 2005 1 0035266

(51) Int. Cl.
G01N 21/35    (2006.01)
(52) U.S. Cl. .............................. 250/339.13; 250/339.06; 250/341.1; 250/343
(58) Field of Classification Search ............ 250/339.13, 250/339.01, 339.06, 339.12, 341.1, 343
See application file for complete search history.

(56) References Cited

U.S. PATENT DOCUMENTS

| | | | | |
|---|---|---|---|---|
| 4,069,420 | A | * | 1/1978 | Ross ........................ 250/341.5 |
| 4,163,899 | A | * | 8/1979 | Burough ..................... 250/343 |
| 4,393,304 | A | | 7/1983 | Ishida et al. |
| 4,510,389 | A | | 4/1985 | Fumoto |
| 4,692,621 | A | | 9/1987 | Passaro et al. |
| 4,914,719 | A | | 4/1990 | Conlon et al. |
| 4,958,076 | A | * | 9/1990 | Bonne et al. ................. 250/343 |
| 5,046,018 | A | | 9/1991 | Flewelling et al. |
| 5,063,275 | A | | 11/1991 | Rosenfeld et al. |
| 5,070,245 | A | * | 12/1991 | Rantala et al. .............. 250/343 |
| 5,081,998 | A | * | 1/1992 | Yelderman et al. .......... 600/532 |
| 5,095,913 | A | * | 3/1992 | Yelderman et al. .......... 600/532 |

(Continued)

FOREIGN PATENT DOCUMENTS

CN    2205005 Y    8/1995

(Continued)

OTHER PUBLICATIONS

Chinese Office Action CN 200510035266.0.

*Primary Examiner*—David P Porta
*Assistant Examiner*—David S Baker
(74) *Attorney, Agent, or Firm*—Vista IP Law Group, LLP

(57)    ABSTRACT

Disclosed is a method and apparatus for detecting the type of anesthetic gas. The method comprises the steps of: generating a light with a plurality of wavelengths, the light being able to be separated to a plurality of light beams whose central frequencies correspond to the plurality of wavelengths; passing said light through a gas chamber, wherein, the gas chamber being filled with said anesthetic gas, said anesthetic gas having absorption characteristic with respect to said plurality of light beams; detecting the light intensity of the attenuated light beams transmitted from the gas chamber respectively, to obtain the relative absorption characteristic of said attenuated light beams, which attenuated light beams having been absorbed by said anesthetic gas; and determining the type of said anesthetic gas based on the relative absorption characteristic between said attenuated light beams.

20 Claims, 3 Drawing Sheets

U.S. PATENT DOCUMENTS

| | | | |
|---|---|---|---|
| 5,130,544 A * | 7/1992 | Nilsson | 250/343 |
| 5,231,591 A | 7/1993 | Flewelling et al. | |
| 5,281,817 A * | 1/1994 | Yelderman et al. | 250/343 |
| 5,296,706 A * | 3/1994 | Braig et al. | 250/339.13 |
| 5,585,635 A * | 12/1996 | Graham | 250/343 |
| 5,731,581 A * | 3/1998 | Fischer et al. | 250/339.13 |
| 5,739,535 A * | 4/1998 | Koch et al. | 250/339.13 |
| 5,920,069 A * | 7/1999 | Fischer et al. | 250/339.13 |
| 5,942,755 A * | 8/1999 | Dreyer | 250/339.13 |
| 6,545,278 B1 * | 4/2003 | Mottier et al. | 250/339.13 |
| 6,955,652 B1 * | 10/2005 | Baum et al. | 600/532 |
| 7,132,658 B2 * | 11/2006 | Weckstrom et al. | 250/339.13 |

FOREIGN PATENT DOCUMENTS

| | | |
|---|---|---|
| CN | 1147633 A | 4/1997 |
| WO | 9004164 | 4/1990 |

\* cited by examiner

METHOD AND APPARATUS FOR DETECTING THE TYPE OF ANESTHETIC GAS

FIELD OF THE INVENTION

The invention relates to a method and apparatus for detecting the type of gas, and more particularly, to a method and apparatus for detecting the type of anesthetic gas.

BACKGROUND OF THE INVENTION

In medical field, the anesthetic gases are commonly used to assist the treatment. With respect to different kinds of anesthetic gases, different concentrations must be adopted to meet the requirements of the clinical medicine, based on the age and the physical condition of the patient.

In the commonly used anesthetic instruments, the type of the anesthetic gas is generally manually input by the anesthetist, and the operation is extremely inconvenient. In recent years, attempts are being made to propose a practical method and apparatus for automatically identifying the type of anesthetic gas with high accuracy.

The measuring principle of the conventional method for identifying the type of anesthetic gases is generally based on the Non-dispersive Infrared (NDIR) technique. That is, by utilizing the characteristic that a certain gas exhibits absorption effect with respect to a certain wave band and passing infrared light waves of the wave band through gas sample to be detected, the type of the anesthetic gas is determined by solving a matrix equation utilizing the theory that the attenuated amount of the transmissive lights and the concentration of the gas to be detected satisfy the Beer-Lambert law.

However, the infrared absorption spectrums of commonly used anesthetic gases in clinic medicine (i.e. Desflurane, Isoflurane, Halothane, Sevoflurane, Enflurane) are concentrated within a wide range of 7-14 µm and overlapped with each other. Moreover, the Beer-Lambert law is applicable to monochromatic light. In practice, however, the infrared lights filtered by light filters from the infrared light source generally have a certain bandwidth.

Therefore, the above-mentioned matrix equation will become a non-linear matrix equation when the type of the gas to be detected is determined by utilizing the Beer-Lambert law, which makes the solving procedure extremely complicated.

Although the non-linear matrix equation can be simplified by performing a particular design with respect to the parameters of light filters (see U.S. Pat. Nos. 5,046,018, 5,231,591), the design and the manufacturing process for the light filters is of great complexity, resulting a rise in the cost of the apparatus for detecting anesthetic gases utilizing the light filters.

SUMMARY OF THE INVENTION

An object of the present invention is to provide a method and apparatus capable of determining the type of anesthetic gas automatically. An advantage of the method and apparatus is that the complexity is low and the cost is reduced.

A method for detecting the type of anesthetic gas according to the present invention, comprises the steps of: generating a light with a plurality of wavelengths, the light being able to be separated to a plurality of light beams whose central frequencies correspond to the plurality of wavelengths; passing said light through a gas chamber, wherein, the gas chamber being filled with said anesthetic gas, said anesthetic gas having absorption characteristic with respect to said plurality of light beams; detecting the light intensity of the attenuated light beams transmitted from the gas chamber respectively, to obtain the relative absorption characteristic of said attenuated light beams, which attenuated light beams having been absorbed by said anesthetic gas; and determining the type of said anesthetic gas based on the relative absorption characteristic between said attenuated light beams.

An apparatus for detecting the type of anesthetic gas according to the present invention, comprises: at least a light source, operative to generate a light with a plurality of wavelengths, the light being able to be separated to a plurality of light beams whose central frequencies correspond to the plurality of wavelengths; a gas chamber, to which said anesthetic gas is injected, wherein, said anesthetic gas having absorption characteristic with respect to said plurality of light beams having passed through said gas chamber; a detecting unit, operative to detect the light intensity of the attenuated light beams transmitted from the gas chamber respectively, in order to obtain the relative absorption characteristic between said attenuated light beams, which attenuated light beams having been absorbed by said anesthetic gas; and a determining unit, operative to determine the type of said anesthetic gas based on the relative absorption characteristic between said attenuated light beams.

Other objects and results of the present invention will become more apparent and will be easily understood with reference to the description made in combination with the accompanying drawings.

BRIEF DESCRIPTION OF THE DRAWINGS

The present invention will be described and explained hereinafter in more detail in combination with embodiments and with reference to the drawings, wherein.

Figure 1:
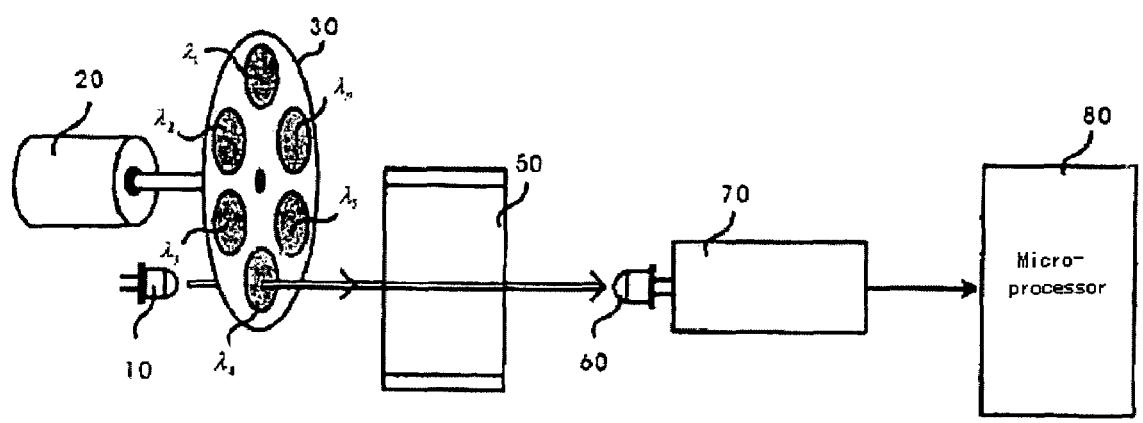
FIG. 1 shows a schematic view of the structure of an apparatus for detecting the type of anesthetic gas according to an embodiment of the invention.

The same reference signs in the figures indicate similar or corresponding feature and/or functionality.

BEST MODE FOR CARRYING OUT THE PRESENT INVENTION

The method for detecting the type of anesthetic gas according to the present invention is realized in that: in view of the characteristic that an anesthetic gas exhibits absorption effect with respect to infrared lights of different wavelengths, passing the infrared lights through the anesthetic gas to be detected, the type of the anesthetic gas will then be determined by utilizing the relative absorption coefficients between respective attenuated light beams obtained from the Beer-Lambert law and based on the particular relationship between said relative absorption coefficients.

Initially, in accordance with the Beer-Lambert law, when light beam of a certain wavelength (for example: $\lambda_n$) passes through a gas chamber into which anesthetic gas A is injected, the light intensity $I_n$ of the transmissive light beam and the light intensity $I_{0n}$ of the incident light beam satisfy the equation below:

$$\frac{I_n}{I_{0n}} = e^{-k_{An}C_A l} \qquad \text{Equation (1)}$$

where, $k_{An}$ represents the infrared spectrum absorption coefficient of the infrared light beam with wavelength $\lambda_n$ for the anesthetic gas A, $C_A$ represents the concentration of the anesthetic gas A in the gas chamber, and l is the length of the chamber.

The equation (1) will be simplified to the equation below on assumption that $a_n = k_{An} \cdot l$:

$$\frac{I_n}{I_{0n}} = e^{-a_n C_A} \qquad \text{Equation (2)}$$

If both sides of the Equation (2) are subjected to natural logarithm, the following is then obtained:

$$\ln(I_{0n}/I_n) = a_n \cdot C_A \qquad \text{Equation (3)}$$

Thereafter, sequentially passing a plurality of light beams of various wavelengths, e.g. $\lambda_1$, $\lambda_2$, $\sim\lambda_n$, through the gas chamber injected with the anesthetic gas A.

Assumed that the infrared spectrum absorption coefficients of the infrared light beams of different wavelengths with respect to the anesthetic gas A are $k_{A1}$, $k_{A2}$, $\sim k_{An}$ respectively, and $a_1 = k_{A1} \cdot l$, $a_2 = k_{A2} \cdot l$, $\sim a_n = k_{An} \cdot l$, the following set of equations each corresponding to each of the infrared light beams of different wavelengths will be obtained from the Equation (3):

$$\ln(I_{01}/I_1) = a_1 \cdot C_A$$
$$\ln(I_{02}/I_2) = a_2 \cdot C_A$$
$$\vdots$$
$$\ln(I_{0n}/I_n) = a_n \cdot C_A$$

Taking either of the above set of equations as a reference, dividing the rest of the equations by the selected one, finally, the effect of the concentration of the anesthetic gas A is eliminated, and the relative absorption coefficients between various infrared light beams of different wavelengths for the anesthetic A are eventually attained.

For example, if the second equation of the above set of equations is taken as the reference, the rest of the equations are divided by the second equation respectively, then $$\frac{\ln(I_{01}/I_1)}{\ln(I_{02}/I_2)} = a_1/a_2$$
$$\vdots$$
$$\frac{\ln(I_{0n}/I_n)}{\ln(I_{02}/I_2)} = a_n/a_2$$

The above equations each indicate the relative absorption coefficients of infrared light beams of various wavelengths relative to the infrared light beam of wavelength $\lambda_2$ with respect to the anesthetic gas A.

For different kinds of anesthetic gases, the relative absorption coefficients of infrared light beams of various wavelengths relative to either one of the infrared light beams therein are of particular relationship, therefore, the type of the anesthetic gas may be determined in accordance with the relative absorption coefficients of infrared light beams of various wavelengths relative to either one of the infrared light beams therein.

Based on the above theory, the present invention proposes a practical method and apparatus for detecting the type of anesthetic gas with high accuracy.

Hereinafter, an apparatus for detecting the type of anesthetic gas according to an embodiment of the present invention will be firstly described with reference to FIG. 1.

As shown in FIG. 1, the apparatus for detecting the type of anesthetic gas according to the present invention, comprises: a infrared light source 10; a light filter wheel 30 provided with a plurality of light filters, wherein, the light filter wheel may be driven to rotate by an electromotor 20, and the light beam filtered out by each of the light filters is a light beam having a central frequency and the bandwidth thereof within a predetermined range (the bandwidth $\Delta\lambda$ is less than 200 nm, preferably less than 90 nm); a detection gas chamber 50 into which the anesthetic gas to be detected is injected, wherein, the infrared light of wide band generated by the light source 10 sequentially pass through the gas chamber 50 after having been filtered by the various light filters provided on the light filter wheel 30; a infrared light sensor 60 for respectively detecting the light intensities of various attenuated light beams transmitted through the gas chamber 50, which attenuated light beams having been absorbed by the anesthetic gas; a signal amplifying processing circuit 70 to amplify the signals detected by the infrared light sensor 60; a microprocessor 80, which calculates the relative absorption coefficients of infrared light beams of various wavelengths relative to the infrared light beam of a certain wavelength therein with respect to he anesthetic gas based on the amplified signals and determines the type of the anesthetic gas in accordance the particular relationship between the relative absorption coefficients. Wherein, the determination process performed by the microprocessor 80 will be described hereinafter in detail with reference to FIG. 3.

In the apparatus for detecting the type of anesthetic gas of the present invention shown in FIG. 1, it is preferable that the above configuration components are disposed in such a manner that the axis of the infrared light source 10 passes through the center of the light filters and superposes with the axes of the detection gas chamber 50 and infrared light sensor 60, to improve the detection precision of the infrared light sensor 60.

In the embodiment of the present invention shown in FIG. 1, six light filters are provided on the light filter wheel 30, wherein, the infrared light beams $\lambda_1$ to $\lambda_5$, which are filtered by five light filters of wavelength 8.37 µm, 8.55 µm, 8.75 µm, 9.62 µm and 12.3 µm, all exhibit infrared light absorption effect when passing through five anesthetic gases commonly used in current medicine; while the infrared light beam which is filtered by another light filter of wavelength 10.5 µm exhibits substantially no infrared light absorption spectrum when passing through the five anesthetic gases.

Figure 2:
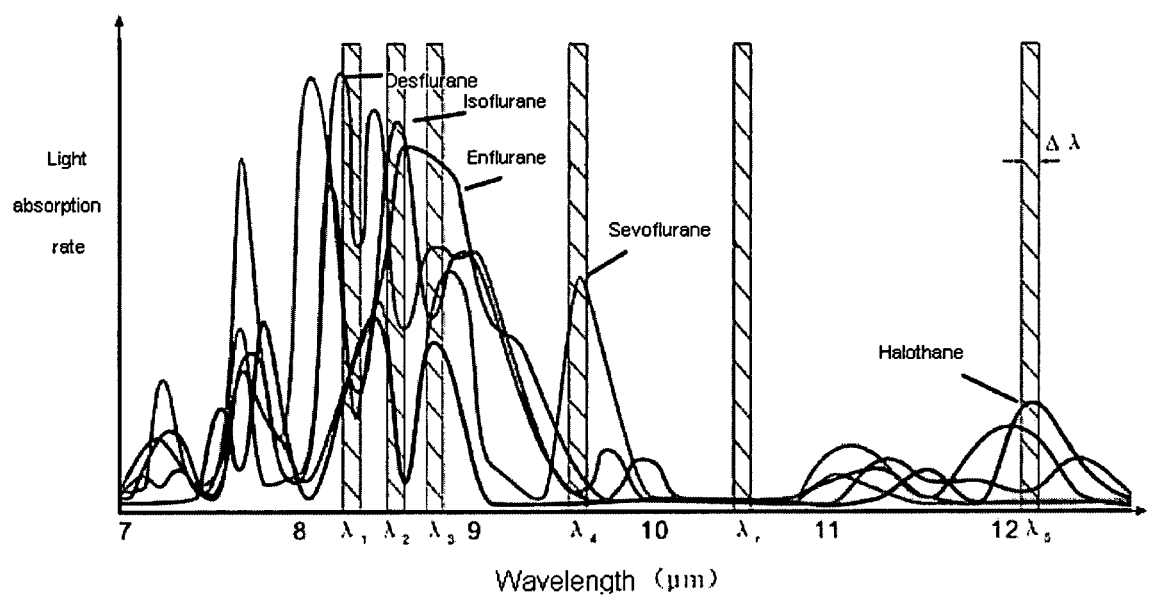
FIG. 2 shows a schematic view of the infrared absorption spectrum of various gases in the embodiment of the present invention.

With reference to FIG. 2, where, $\lambda_r$ represents the infrared light beam which exhibits substantially no infrared light absorption spectrum. In the present invention, the light filter of wavelength $\lambda_r$ is provided to provide a reference light beam in the process of detecting the anesthetic gas, that is, the light intensity of the reference light beam which has been transmitted through the gas chamber 50 may be used as a reference for the light intensity of infrared light generate by the infrared light source 10 in real time, in order to perform calibration to the attenuated light beams transmitted through the gas chamber 50 which have been absorbed by the anesthetic gas, so that the detection precision is further improved.

Figure 3:
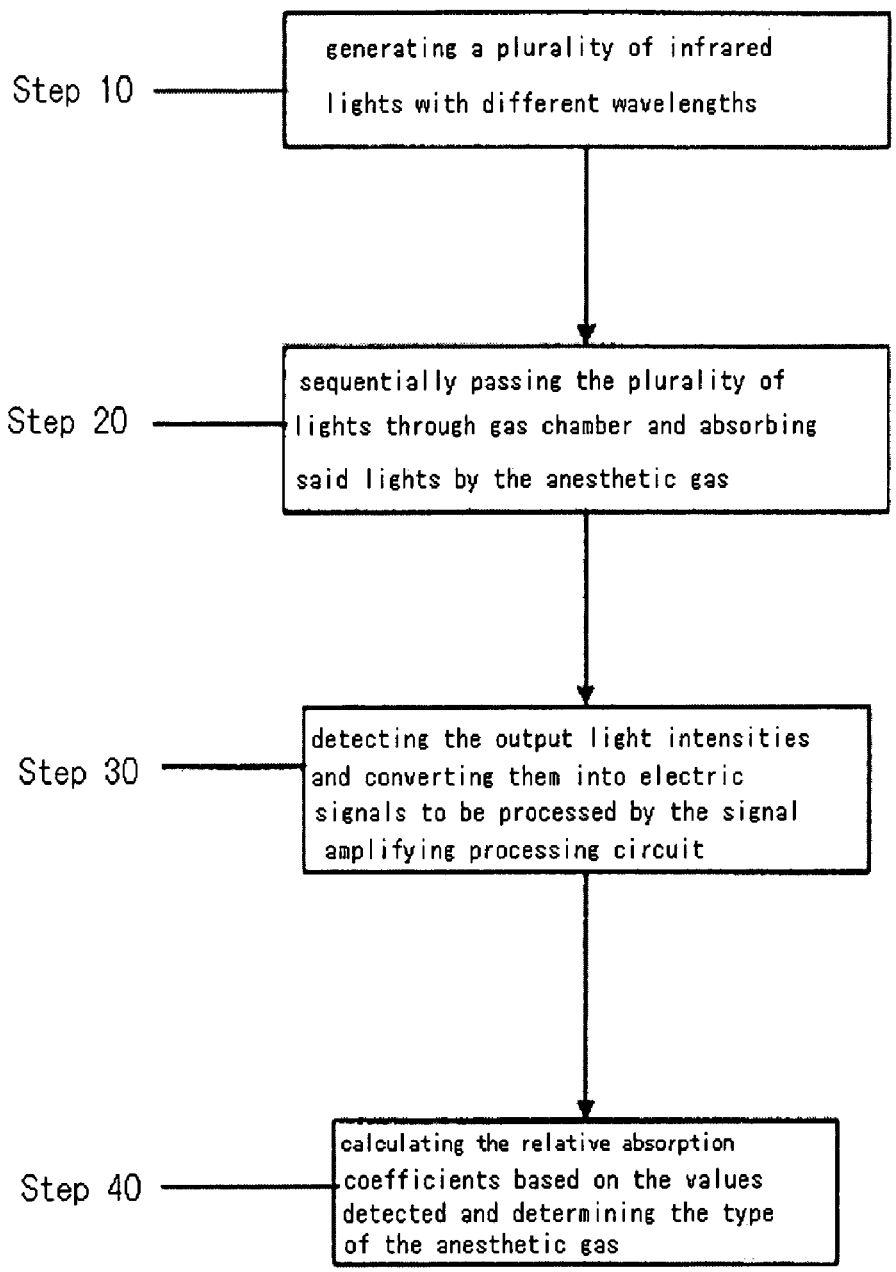
FIG. 3 is a flowchart of a method for detecting the type of anesthetic gas according to the embodiment of the invention.

Hereinafter, a method for detecting the type of anesthetic gas carried out by the apparatus will be described in detail with reference to FIG. 3.

At first, the light filter wheel 30 aligns the respective light filters with the infrared light source 10 in turn under the driving of the electromotor 20, so as to filter out a plurality of infrared light beams whose central frequencies correspond to different wavelengths such as the infrared light beams of wavelengths $\lambda_1$ to $\lambda_5$ and $\lambda_r$ in the above embodiment of the invention (Step S10).

The plurality of light beams sequentially pass through the gas chamber 50 injected with a kind of anesthetic gas; the anesthetic gas exhibits absorption effect to some extent with respect to the infrared light beams except the reference light beam of wavelength $\lambda_r$ (Step S20).

Next, the infrared light sensor 60 detects the light intensities of the various transmissive light beams from the detection gas chamber 50 respectively, and converts the light intensities of various transmissive light beams to electric signals so as to be provided to the signal amplifying processing circuit 70 (Step S30). Wherein, the transmissive light beams include the various attenuated infrared light beams which have been absorbed by the anesthetic gas, and the reference light beam which substantially has not been absorbed by the anesthetic gas.

After the amplifying process performed by the signal amplifying processing circuit 70, the microprocessor 80 calculates the relative absorption coefficients between the various attenuated light beams based on the detected light intensities of the various attenuated light beams, so as to determine the type of the anesthetic gas (Step S40).

The steps performed by the microprocessor 80 comprise: calculating the relative absorption coefficients of the various attenuated light beams relative to either of the attenuated light beams therein, respectively. In the embodiment of the present invention, the relative absorption coefficients of the various attenuated light beams of wavelengths $\lambda_1$, $\lambda_2$, $\lambda_3$, $\lambda_4$ and $\lambda_5$ relative to the attenuated light beam of wavelength $\lambda_2$ are calculated respectively, i.e., the relative absorption coefficients of $\lambda_1$, $\lambda_2$, $\lambda_3$, $\lambda_4$, $\lambda_5$ relative to $\lambda_2$, respectively.

Thereafter, the microprocessor 80 performs comparison between the values of the various relative absorption coefficients calculated, and determines the type of the anesthetic gas in accordance with the particular relationship between the various relative absorption coefficients. Specifically:

When the relative absorption coefficient of $\lambda_1$ relative to $\lambda_2$ is the maximum and the relative absorption coefficient of $\lambda_4$ relative to $\lambda_2$ is not greater than 1, it is determined that the anesthetic gas is Desflurane;

When the relative absorption coefficient of $\lambda_2$ relative to $\lambda_2$ is the maximum, it is determined that the anesthetic gas is Isoflurane;

When the relative absorption coefficient of $\lambda_3$ relative to $\lambda_2$ is the maximum, it is determined that the anesthetic gas is Enflurane;

When the relative absorption coefficient of $\lambda_4$ relative to $\lambda_2$ is greater than 1, it is determined that the anesthetic gas is Sevoflurane;

When the relative absorption coefficient of $\lambda_5$ relative to $\lambda_2$ is the maximum and the numerical value of which is greater than a predetermined value (for example: 0.2), while the relative absorption coefficients of other wavelengths relative to $\lambda_2$ are approximate to zero (for example: the relative absorption coefficient of $\lambda_4$ relative to $\lambda_2$ is not greater than 0.1), it is determined that the anesthetic gas is Halothane.

In addition, the above various relative absorption coefficients and the comparison result there between also can be coded with reference to a predetermined value, so that the microprocessor 80 may send the coded information about the type of the detected anesthetic gas to conventional display.

For example, a byte comprising five bits (binary bit) may be used to represent the code. The value of each bit of the byte is set as follows:

When the relative absorption coefficient of $\lambda_1$ relative to $\lambda_2$ is the maximum, it is set that Bit0=1;

When the relative absorption coefficient of $\lambda_2$ relative to $\lambda_2$ is the maximum, it is set that Bit1=1;

When the relative absorption coefficient of $\lambda_3$ relative to $\lambda_2$ is the maximum, it is set that Bit2=1;

When the relative absorption coefficient of $\lambda_4$ relative to $\lambda_2$ is greater than 1, it is set that Bit3=1, otherwise, Bit3=0;

When the relative absorption coefficient of $\lambda_5$ relative to $\lambda_2$ is greater than a predetermined value, while the relative absorption coefficients of other wavelengths relative to $\lambda_2$ are all less than another predetermined value, it is set that Bit4=1.

As can be seen from the above determination rules, when Bit1, Bit2, Bit3 and Bit4 are 1 respectively, it is determined that the detected anesthetic gas is Isoflurane, Enflurane, Sevoflurane and Halothane respectively. While Bit0=1 and Bit3=0, it indicates that the detected anesthetic gas is Desflurane.

Based on the values of the corresponding bits that have been sent, the conventional display may display the type of the detected anesthetic gas to the doctor to assist his operation in the therapy procedure.

Advantageous Effects

Since the method and apparatus for detecting the type of anesthetic gas according to the present invention is realized in that: in view of the characteristic that an anesthetic gas exhibits absorption effect with respect to infrared lights of different wavelengths, passing the infrared lights through the anesthetic gas to be detected, the type of the anesthetic gas will then be determined by utilizing the relative absorption coefficients between respective attenuated light beams obtained from the Beer-Lambert law and based on the particular relationship between said relative absorption coefficients. Thus, it is not necessary to obtain the concentration of the gas in the present invention, so that the procedure of solving the non-linear matrix equation is avoided and the particular design for the light filters is no longer necessary, as a result, the complexity and cost of the apparatus is further reduced.

In practical application, the technical solution disclosed by the invention may be freely applied and adaptively modified according to the requirement.

For example, the step of calculating the relative absorption coefficients between various attenuated infrared light beams based on the light intensities of various attenuated infrared light beams detected and determining the type of the anesthetic gas performed by the microprocessor 80 may be implemented by software, or it may be implemented by hardware or further in a manner software and hardware are combined.

Moreover, in the embodiment of the present invention, the type of the anesthetic gas may be detected by utilizing the infrared spectrum absorption characteristic of the anesthetic gas, and it also may be detected by utilizing the spectrum absorption characteristic of the anesthetic gas in other wave bands.

While the present invention utilizes a light filter wheel provided with light filters to filter out a plurality of light beams whose central frequencies correspond to different wavelengths, it is also possible to directly use independent light sources which generate various light beams of different wavelengths to achieve this purpose.

Furthermore, the light filter wheel adopted in the present invention may be disposed in front of the gas chamber, to sequentially pass the various attenuated light beams corresponding to the various light filters through the gas chamber, so that the sensor can perform detection with respect to the light intensities of various attenuated light beams transmitted through the gas chamber respectively; the light filter wheel also may be disposed following the gas chamber, to sequentially filter the plurality of attenuated light beams which have passed through the gas chamber, so that the sensor is capable of detecting the light intensities of various attenuated light beams respectively.

While the present invention utilizes the relative absorption coefficient to determine the type of the anesthetic gas detected, it is also possible to determine the type of the anesthetic gas on the basis of other absorption characteristics.

It should be understood by the skilled persons in the art, many modifications and changes might be made to the method and apparatus for detecting the type of anesthetic gas disclosed above by the present invention without departing from the contents of the invention. Accordingly, the protection scope of the present invention is defined by the claims.

Although the present invention has been described in connection with the preferred embodiment, it is not intended to be limited to the specific form set forth herein. Rather, the scope of the present invention is limited only by the accompanying claims. In the claims, the term comprising does not exclude the presence of other elements or steps. Furthermore, although individually listed, a plurality of means, elements or method steps may be implemented by e. g. a single unit or processor. Additionally, although individual features may be included in different claims, these may possibly be advantageously combined, and the inclusion in different claims does not imply that a combination of features is no feasible and/or advantageous.

What is claimed is:

1. A method for detecting a type of anesthetic gas, comprising:
   generating a light with a plurality of wavelengths, the light comprising a plurality of light beams with central frequencies corresponding to the plurality of wavelengths;
   passing said light through a gas chamber, wherein the gas chamber is filled with said type of anesthetic gas, and said type of anesthetic gas has an absorption characteristic with respect to said plurality of light beams;
   detecting a light intensity of each of the plurality of light beams transmitted through the gas chamber to obtain a relative absorption coefficient between selected two of said plurality of light beams attenuated, wherein the plurality of light beams are absorbed by said type of anesthetic gas and are attenuated; and
   determining the type of anesthetic gas based on the relative absorption coefficient between the selected two of said plurality of attenuated light beams without determining or identifying a concentration of the anesthetic gas.

2. A method according to claim 1, wherein the act of determining the type of anesthetic gas comprises:
   calculating the relative absorption coefficient based on the relative absorption characteristic;
   identifying the type of said anesthetic gas based at least in part upon said relative absorption coefficient.

3. A method according to claim 2, wherein, said light is infrared light.

4. A method according to claim 3, wherein, said wavelengths comprise: 8.37 μm, 8.55 μm, 8.75 μm, 9.62 μm, and 12.3 μm.

5. A method according to claim 4, wherein, said relative absorption coefficient relative to wavelength of 8.55 μm are calculated respectively.

6. A method according to claim 2, further comprising:
   encoding said relative absorption coefficient; and
   sending an encoded information concerning the type of said anesthetic gas.

7. A method according to claim 6, wherein the act of encoding said relative absorption coefficient comprises:
   setting a threshold value for the relative absorption coefficient and a determination criteria, wherein if the relative absorption coefficient is larger than the threshold value, setting a corresponding bit in a coding byte as 1, otherwise, as 0.

8. A method according to claim 6, wherein the act of encoding said relative absorption coefficient comprises:
   comparing a magnitude of the relative absorption coefficient with a first magnitude of another one or more relative absorption coefficients, wherein if a certain relative absorption coefficient is maximum, setting the corresponding bit in a coding byte as 1, otherwise, as 0.

9. A method according to claim 6 wherein the act of encoding said relative absorption coefficient comprises:
   where the relative absorption coefficient is maximum and another particular relative absorption coefficient is minimum, setting the corresponding bit in a coding byte as 1, otherwise, as 0.

10. The method according to claim 1, wherein the act of generating a light comprises:
    filtering said light by utilizing a plurality of light filters corresponding to said central frequencies in order to sequentially pass the plurality of light beams each of which corresponds to one of said respective light filters through said gas chamber.

11. The method according to claim 1, wherein the act of detecting one or more light intensities comprises:
    filtering said light utilizing a plurality of light filters corresponding to said central frequencies respectively in order to separately detect the each of the plurality of light beams that corresponds to a respective light filter of the plurality of light filters.

12. A method according to claim 1, further comprising:
    generating a reference light beam;
    passing the reference light beam through said gas chamber filled with said anesthetic gas, wherein said anesthetic gas exhibits substantially no absorption characteristic with respect to said reference light wave; and
    calibrating said light intensity of said each of the plurality of light beams which are attenuated after being transmitted through said gas chamber by utilizing said reference light beam as a reference.

13. An apparatus for detecting a type of anesthetic gas, comprising:
    at least one light source configured for generating a light with a plurality of wavelengths, the light being separated to a plurality of light beams whose central frequencies correspond to the plurality of wavelengths;
    a gas chamber, to which said anesthetic gas is injected, wherein said type of anesthetic gas has an absorption characteristic with respect to one of said plurality of light beams having passed through said gas chamber;
    a detecting unit configured for detecting light intensity of the one of the plurality of light beams transmitted through the gas chamber to obtain a relative absorption coefficient between the one of the plurality of light beams and another light beam of the plurality of light beams, wherein the light beams are absorbed by said anesthetic gas after being injected into the gas chamber; and a determining unit configured for determining the type of said anesthetic gas based at least in part on the relative absorption coefficient without determining or identifying a concentration of the anesthetic gas.

14. An apparatus according to claim 13, wherein said determining unit further comprises:

a calculating unit configured for calculating the relative absorption coefficient based on the relative absorption characteristic;

an identifying unit configured for identifying the type of said anesthetic gas based at least upon said relative absorption coefficient.

15. An apparatus according to claim 14, wherein, said light source is operative to generate infrared lights and said wavelengths comprise: 8.37 μm, 8.55 μm, 8.75 μm, 9.62 μm and 12.3 μm.

16. An apparatus according to claim 15, wherein, said relative absorption coefficient relative to the wavelength of 8.55 μm are calculated respectively.

17. An apparatus according to claim 14, further comprising:

an encoding unit configured for coding said relative absorption coefficient so as to send an information about the type of said anesthetic gas.

18. An apparatus according to claim 13 further comprises:

a plurality of light filters corresponding to said central frequencies being configured to filter said light to pass one of the plurality of light beams which corresponds respectively to one of said light filters through said gas chamber sequentially.

19. An apparatus according to claim 13, further comprises:

a plurality of light filters corresponding to said central frequencies to respectively filter said light having passed through said gas chamber in order to separately detect a respective attenuated light beam which corresponds to one of the plurality of light filters.

20. An apparatus according to claim 13, further comprises:

an unit configured for generating a reference light beam to calibrate the light intensity of said one of the plurality of light beams transmitted through said gas chamber by utilizing a reference light beam as a reference, wherein said anesthetic gas substantially exhibiting no absorption characteristic with respect to said reference light beam.

* * * * *